US007610098B2

(12) United States Patent
McLean

(10) Patent No.: US 7,610,098 B2
(45) Date of Patent: Oct. 27, 2009

(54) CHARGE-INTEGRATING RETINAL PROSTHESIS AND METHOD

(75) Inventor: George Y. McLean, Menlo Park, CA (US)

(73) Assignee: IMI Intelligent Medical Implants AG, Zug (CH)

( * ) Notice: Subject to any disclaimer, the term of this patent is extended or adjusted under 35 U.S.C. 154(b) by 353 days.

(21) Appl. No.: 11/313,245

(22) Filed: Dec. 20, 2005

(65) Prior Publication Data

US 2007/0142877 A1 Jun. 21, 2007

(51) Int. Cl.
*A61N 1/00* (2006.01)
(52) U.S. Cl. ........................................ 607/53
(58) Field of Classification Search ............ 607/53; 257/292
See application file for complete search history.

(56) References Cited

U.S. PATENT DOCUMENTS 5,942,775 A * 8/1999 Yiannoulos ............... 257/292
6,427,087 B1 * 7/2002 Chow et al. ............... 607/54

FOREIGN PATENT DOCUMENTS

WO 03/002070 A2 1/2003
WO 03-061537 A1 7/2003
WO 2005/070495 A1 8/2005

OTHER PUBLICATIONS

Palanker D, et al., "Design of a High-Resolution Optoelectronic Retinal Prosthesis", Journal of Neural Engineering IOP Publishing, UK, vol. 2, No. 1, Mar. 2005.
DeGuchi J. et al., "Three-Dimensionally Stacked Analog Retinal Prosthesis Chip", Japanese Journal of Applied Physics, Japan Society of Applied Physics, Tokyo, JP, vol. 43, No. 4B, Apr. 2004.
Sfelzle M. et al., "Electrical properties of micro-photodiode arrays for use as artificial retina implant", Biomedical Microdevices Kluwer Academic Publishers USA, vol. 3, No. 2, 2001.

* cited by examiner

*Primary Examiner*—George Manuel
(74) *Attorney, Agent, or Firm*—Foley & Lardner LLP

(57) ABSTRACT

A retinal prosthesis that provides power control capabilities through the temporal integration of electrical charge is provided. The retinal prosthesis comprises at least one stimulating component, each stimulating component in turn comprising a photojunction element (e.g., a photodiode) in electrical communication with an electrode. A pulse generation circuit provides a reverse-bias signal and, from time to time, a pulsatile forward-bias signal to the photojunction element. During application of the reverse-bias signal, light incident upon the photojunction element causes electrical charge to be accumulated. Upon application of the pulsatile forward-bias signal, the accumulated electrical charge is injected via the electrode into retinal tissues, thereby stimulating the retina. By appropriately selecting the bias signal parameters, a sufficient amount of charge may be accumulated to ensure reaching stimulation thresholds. In this manner, control over stimulus currents may be improved while still retaining advantageous use of the eye's natural focusing and imaging capabilities.

21 Claims, 5 Drawing Sheets

CHARGE-INTEGRATING RETINAL PROSTHESIS AND METHOD

FIELD OF THE INVENTION

The present invention relates generally to retinal prostheses and, in particular, to a retinal prosthesis configured to integrate charge resulting from photoconduction caused by incident light.

BACKGROUND

Many human retinal diseases cause vision loss by partial to complete destruction of the vascular layers of the eye that include the choroid and choriocapillaris, both of which nourish the outer anatomical retina and a portion of the inner anatomical retina of the eye.

Many other retinal diseases cause vision loss due to partial to complete degeneration of one or both of the two anatomical retinal layers directly, due to inherent abnormalities of these layers. The components of the retinal layers include Bruch's membrane and retinal pigment epithelium which comprise the "outer anatomical retinal layer", and the photoreceptor, outer nuclear, outer plexiform, inner nuclear, inner plexiform, amacrine cell, ganglion cell and nerve fiber layers which comprise the "inner anatomical retinal layer", also known as the "neuroretina". The outer portion of the neuroretina is comprised of the photoreceptor and bipolar cell layers and is also known as the "outer retina" which is to be distinguished from the "outer anatomical retinal layer" as defined above. Loss of function of the outer retina is commonly the result of dysfunction of the outer anatomical retinal layer that provides nourishment to the outer retina and/or direct defects of the outer retina itself. The final common result is dysfunction of the outer retina that contains the light sensing cells, the photoreceptors. These "outer retina" diseases include age-related macula degeneration, retinitis pigmentosa, choroidal disease, long-term retinal detachment, diabetic retinopathies, Stargardt's disease, choroideremia, Best's disease, and rupture of the choroid. The inner portion of the neuroretina, however, often remains functionally and anatomically quite intact and may be activated by the appropriate stimuli.

There are currently numerous efforts underway to develop prosthetic devices that may be used to replace some degree of visual function to patients with the diseases described above. Many of the approaches are premised on the hypothesis that acute electrical stimulation using an array of stimulation electrodes may be used to form patterned vision. Typically, these approaches rely on relatively complex systems in which a video camera or similar device is used to capture images for subsequent processing and encoding. The encoded information thereafter controls electrical stimulation provided via an array of electrodes implanted proximate to retinal tissues. Typically, the electrode array is implanted epiretinally (on the ganglion cell layer side of the neuroretina) or subretinally (between the outer retina and the outer anatomical retinal layer, as defined above) and is connected through a wired or wireless connection to the appropriate control circuitry. In some instances, the wired connection must traverse the sclera, the tough outer coating of the eye often referred to as the white portion of the eye. Regardless, an advantage of providing such a connection between the control circuitry and the stimulating array is the ability to control the level of electrical stimulation delivered to neural tissues.

However, in addition to being relatively complex, systems of the type described above fail to take advantage of the eye's natural movements and its ability to focus images on the retina. They instead produce stimulation in a pattern not necessarily having any relationship to the eye's spatial orientation.

One approach that does take advantage of the eye's natural movements and focusing ability is the ASR® device developed by Optobionics Corporation. Comprising an array of several thousand electrode-tipped, independent photodiodes, the ASR® device is implanted in the subretinal space of the eye. The photodiodes are designed to essentially mimic the function of missing or non-functioning photoreceptors by converting incident light to electrical stimulation that may be further processed by the remaining retinal cell layers. Because of its simple design, the ASR® device offers several advantages over other, more complex retinal prosthesis systems. While it is believed that the ASR® device can be configured to generate sufficient electrical stimulation to reach stimulation thresholds, thereby inducing neuronal responses, efficacy of the device could be enhanced and perhaps better controlled through the provision of additional power.

Therefore, it would be advantageous to provide a retinal prosthesis that combines the simplicity and ability to exploit natural eye movements of the ASR® device with the power control capability of other, more complex retinal prosthesis systems.

SUMMARY

The present invention comprises a retinal prosthesis that provides power control capabilities through the temporal integration or accumulation of electrical charge. In particular, a retinal prosthesis in accordance with the present invention comprises at least one stimulating component, each stimulating component in turn comprising a photojunction element (e.g., a photodiode) in electrical communication with an electrode. A pulse generation circuit in electrical communication with the photojunction element provides a reverse-bias signal to the photojunction element and, from time to time, provides a pulsatile forward-bias signal to the photojunction element. In a presently preferred embodiment, an array of photojunction elements is provided, which array is electrically coupled to the pulse generation circuit via a common electrode. An at least partially-implanted energy source is used to provide power to the pulse generation circuit. In various embodiments of the present invention, the implanted portion of the energy source as well as the pulse generation circuit may be implanted in an extra-ocular (i.e., within the body but outside the eye) and/or intra-ocular (i.e., within the eye) configuration.

During application of the reverse-bias signal, through the process of photoconduction, light incident upon the photojunction element causes electrical charge to be accumulated over time in a manner akin to the accumulation of charge in a single pixel element of an electronic camera during a single exposure. Upon subsequent application of the pulsatile forward-bias signal, electrical continuity through the photojunction element results, and the accumulated electrical charge is injected via the electrode into retinal tissues adjacent the electrode, thereby stimulating the retina. By appropriately selecting the parameters of the reverse-bias signal, a sufficient amount of charge may be accumulated (and subsequently released by the pulsatile forward-bias signal) to ensure that stimulation thresholds are met. In this manner, control over stimulus currents may be improved while still retaining advantageous use of the eye's natural focusing and imaging capabilities, thereby increasing the probability of successful clinical outcomes.

DETAILED DESCRIPTION OF THE PRESENTLY PREFERRED EMBODIMENTS

Figure 1:
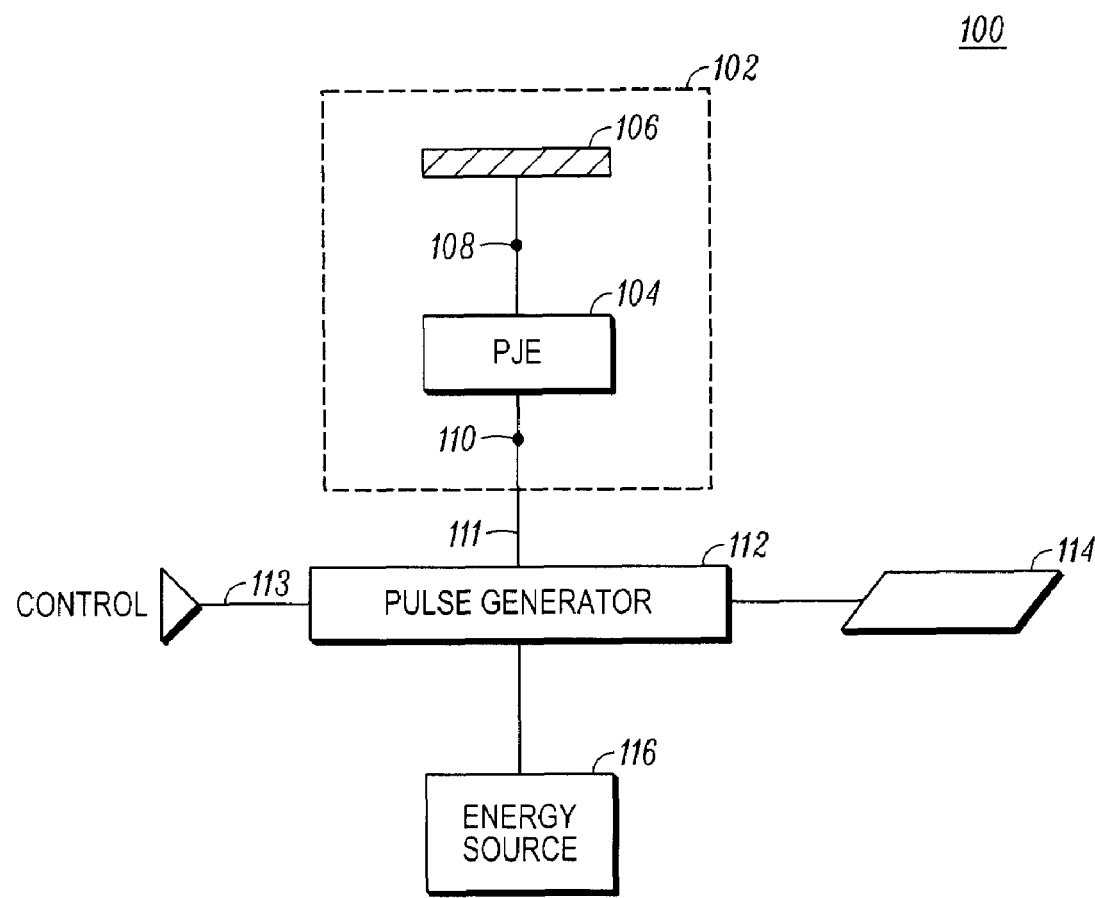
FIG. 1 is a schematic illustration of a retinal prosthesis in accordance with the present invention.

Referring now to FIG. 1, a schematic illustration of a retinal prosthesis 100 in accordance with the present invention is provided. In particular, the retinal prosthesis comprises at least one stimulating component 102 (only one shown) itself comprising a photojunction element 104 in electrical communication with an electrode 106 via a first terminal 108 of the photojunction element 104. In a presently preferred embodiment, an array of stimulating components 102 is provided. The photojunction element 104 is in further electrical communication with a pulse generation circuit (or pulse generator) 112 via a second terminal 110 and a conductive element 111. As described in greater detail below, the conductive element 111 may comprise one or more conductors, such as flexible, electrically-independent wires or conductive traces, configured for entirely intra-ocular implantation or for trans-scleral routing outside the eye. The pulse generation circuit 112 is electrically coupled to a return electrode 114 and to an energy source 116.

In practice, the photojunction element 104 may comprise any device or combination of devices capable of exhibiting distinct modes of (i) photoconduction and (ii) rectification (i.e., one-way conduction). For example, a combination of a photoconductive cell such as a cadmium sulfide cell or a cadmium selenide cell in parallel with a silicon diode would suffice, assuming adequate biocompatible encapsulation. In a preferred embodiment, the required combination of photoconduction and rectification is attained using a photodiode, as known in the art. Such photodiodes operate in a photoconductive mode when reverse-biased, and exhibit appreciable conductance in the opposite direction only when forward-biased. When no bias conditions are externally imposed on a photodiode, it operates in a photovoltaic mode, although such photovoltaic operation is not required for the present invention. An example of a retinal prosthesis incorporating the use of photodiodes is the ASR® device by Optobionics Corporation, which may be used to implement the present invention as described in greater detail below. The ASR® device comprises thousands of electrode-tipped photodiodes formed in an appropriately doped silicon substrate using well known semiconductor processing techniques.

A number of well known materials suitable for delivering charge to biological tissues may be used to provide the electrode 106. Titanium, platinum, iridium and oxides thereof are but a few examples of suitable electrode materials, although iridium oxide is preferred. The electrode 106 is also preferably configured for implantation proximate to retinal tissues. In practice, this implies that the electrodes have dimensions on the order of a few microns to tens of microns while still retaining the ability to provide adequate reversible charge injection to reach stimulation thresholds. The terminals 108, 110 comprise electrically conductive paths; techniques for creating such paths are readily known to those having ordinary skill in the art.

The pulse generation circuit 112 generates a reverse-bias signal and, from time to time, a pulsatile forward-bias signal which signals are used to control operation of the photojunction element. In a presently preferred embodiment, where the photojunction element comprises a photodiode, the reverse-bias signal may comprise a positive voltage (when applied to the cathode terminal of the photodiode) and the pulsatile forward-bias signal may comprise a relatively brief negative voltage (also applied to the cathode terminal). When continuously applied in succession, the reverse-bias and pulsatile forward-bias signals in essence form an asymmetric voltage waveform, such as the one illustrated in, and further described with reference to, FIG. 5. As also described in further detail below, the reverse-bias signal causes the photojunction 104 and electrode 106 to effectively integrate electrical current resulting from the photoconduction induced by incident light upon the photojunction 104. The subsequent forward-bias pulse establishes electrical continuity and thereby allows the accumulated charge to be released via the electrode into the surrounding environment, i.e., retinal tissues. Those having ordinary skill in the art will recognize that a variety of well know circuits may be used for the pulse generation circuit 112, such as appropriately configured multivibrator or oscillator circuits fabricated using discrete components or employing integrated circuits such as the well-known 555 timer IC, where the pulse generation circuit 112 is configured to reside outside the body. In a preferred embodiment, the pulse generation circuit 112 is configured for implantation in the body and is therefore preferably fabricated as a standalone integrated circuit or within the same substrate as the stimulating component 102 such that it may be suitably encapsulated for implantation.

The pulse generation circuit 112 may also comprise one or more control inputs 113 that provide the ability to change the configuration of the reverse-bias and pulsatile forward-bias signals. For example, in certain circumstances, it may be desirable to change the duration of the forward-bias pulses, or to change their amplitude. Techniques for controlling such parameters are well known in the art. Additionally, in order to provide electrical continuity through the entire electrical circuit established by the pulse generation circuit 112, stimulating component 102 and the biological tissue, a remote return electrode 114 is electrically coupled to the pulse generation circuit 112.

The energy source 116 provides power to the pulse generation circuit 112. As described in greater detail with reference to FIG. 2, the energy source may reside entirely outside the body with only wired connections providing the power signal to the pulse generator 112. However, in a preferred embodiment, at least a portion of the energy source is implanted within the body, either extra-ocularly or intra-ocularly.

Figure 2:
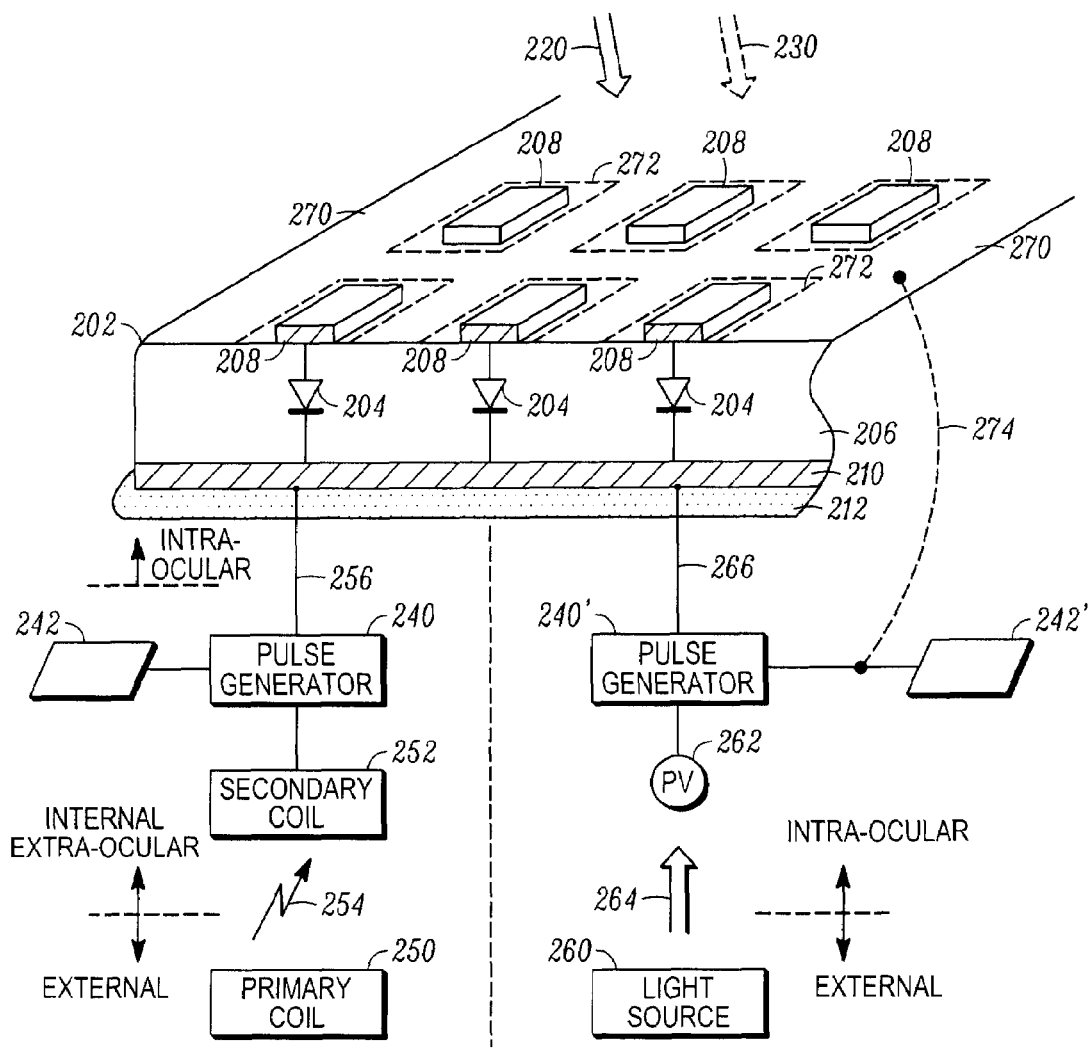
FIG. 2 is a partial cutaway view and schematic illustration of an embodiment of a retinal prosthesis in accordance with the present invention, and further illustrating alternative embodiments of various aspects in accordance with the present invention.

Referring now to FIG. 2, a partial cutaway view and schematic illustration of an embodiment of a retinal prosthesis in accordance with the present invention, and further illustrating alternative embodiments of various aspects in accordance with the present invention, is provided. A photodiode array 202 comprising a plurality of photodiodes 204 formed in a semiconductor substrate 206 (preferably silicon) is provided. As shown, the anode of each photodiode 204 is in electrical communication with a uniquely corresponding electrode 208; as described above, each pairing of photodiode 204 and uniquely corresponding electrode 208 constitutes a stimulating component 102. The electrodes 208 are preferably fashioned out of iridium oxide and are fabricated on a surface of the substrate 206 intended to face incident light 220 and, optionally, any additional light 230 beyond normal, ambient light 220. The cathode of each photodiode 204 is in electrical communication with a common electrode 210, which is preferably fabricated from the same material as the stimulating electrodes 208. Finally, an insulating layer 212 is provided which electrically isolates the common electrode 210 from the environment surrounding the retinal prosthesis, i.e., the conductive ocular environment. Additionally, the insulating layer should be biocompatible and biodurable. Thus, for example, the insulating layer 212 may be fabricated using non-conductive polymers such as parylene, or other materials such as diamond-like carbon. Note that the photodiode array 202 and its constituent elements in FIG. 2 are not shown to scale; the dimensions shown are for illustrative purposes only. Furthermore, additional biocompatibility/biodurability coatings (not shown) may be disposed on those surfaces (other than the stimulating electrodes 208) that would otherwise come into contact with the biological environment, as known in the art.

FIG. 2 also schematically illustrates alternative embodiments for the configuration of the pulse generator 240, 240' and the energy source. For example, as illustrated on the lower left-hand portion of FIG. 2, the energy source is embodied by an inductive coupling system comprising a primary coil 250 that uses electromagnetic signals 254 (typically in the kilohertz to megahertz frequency range) to transfer power via a secondary coil 252 and rectifying circuitry (not shown for ease of illustration). As shown in this example, the primary coil 250 may be configured for external positioning as in the case of a coil mounted anteriorly or temporally on a pair of glasses or goggles. The secondary coil 252 and associated rectifying circuitry are implanted within the body but outside the eye, i.e., extra-ocularly. Such an arrangement of primary and second coils 250, 252 is further described in published patent application WO 03/061537. Likewise, the pulse generator 240 and return electrode 242 are also implanted extra-ocularly. In this case, only the photodiode array 202 and a portion of a trans-scleral conductive element 256 are implanted intra-ocularly. Obviously, in this example, like the photodiode array 202, the other implanted components 240, 252, 256 would need to be encapsulated in an appropriate biocompatible/biodurable coating. Furthermore, although the pulse generator 240, return electrode 242 and secondary coil 252 (and associated circuitry) have been described as configured for extra-ocular placement, it is possible that some or all of these components could be configured for intra-ocular placement as known in the art. For example, as taught by Humayun in published patent application WO 99/45870, the secondary coil and associated rectifying circuitry can be implanted within the eye entirely.

Yet another configuration for an alternative energy source is illustrated in the lower right-hand portion of FIG. 2. In this example, the energy source is embodied by a combination of a light source 260 and a photovoltaic element 262. The light source 260 may comprise any source of light in the relevant portion of the spectrum, preferably in the non-visible range, e.g., an infrared light-emitting diode or an infrared laser. Light 264 is transmitted to the implanted photovoltaic element 262, such as a photodiode, which converts the transmitted light 264 into electrical power that is thereafter provided to the pulse generator 240'. As shown in FIG. 2, the photovoltaic element 262, the pulse generator 240', the return electrode 242' and the conductive element 266 are all implanted intra-ocularly. As in the previous example, however, this is not a necessity as some or all of those components may be implanted extra-ocularly. For example, U.S. Pat. No. 6,427,087 issued to Chow illustrates the use of a photovoltaic element implanted within the anterior chamber or lens capsule of an eye. However, such a photovoltaic element may also be positioned extra-ocularly, for example, on the surface of the sclera but underneath the conjunctiva. In that case, the pulse generator 240' might also be positioned somewhere within the eye's orbit (the bony cavity within which the eye resides) with only a trans-scleral conductive element 266, in addition to the photodiode array 202, positioned within the eye.

One other alternative embodiment is further illustrated in FIG. 2. In particular, rather than using a remote return electrode 242, 242', a return electrode 270 may be incorporated into the photodiode array 202, as illustrated by the dotted lines forming a grid pattern around the stimulating electrodes 208. The electrodes 208 are electrically isolated from the return electrode grid 270 by buffer regions 272 surrounding each electrode 208. In practice, such an arrangement results in a more tightly confined distribution of electrical currents surrounding each stimulating electrode 208, which may provide greater resolution in the pattern of stimulation provided by the retinal prosthesis. Although the electrode grid 270 is illustrated as a continuous, common electrode, it is also possible, though less preferred, to provide more than one return electrode 270 up to and including a uniquely corresponding return electrode for each electrode 208. Regardless, if the return electrode 270 is disposed in such close proximity to the stimulating electrodes 208, one or more additional conductive elements 274 would need to be provided to complete the electrical circuit with the pulse generator 240'.

Figure 3:
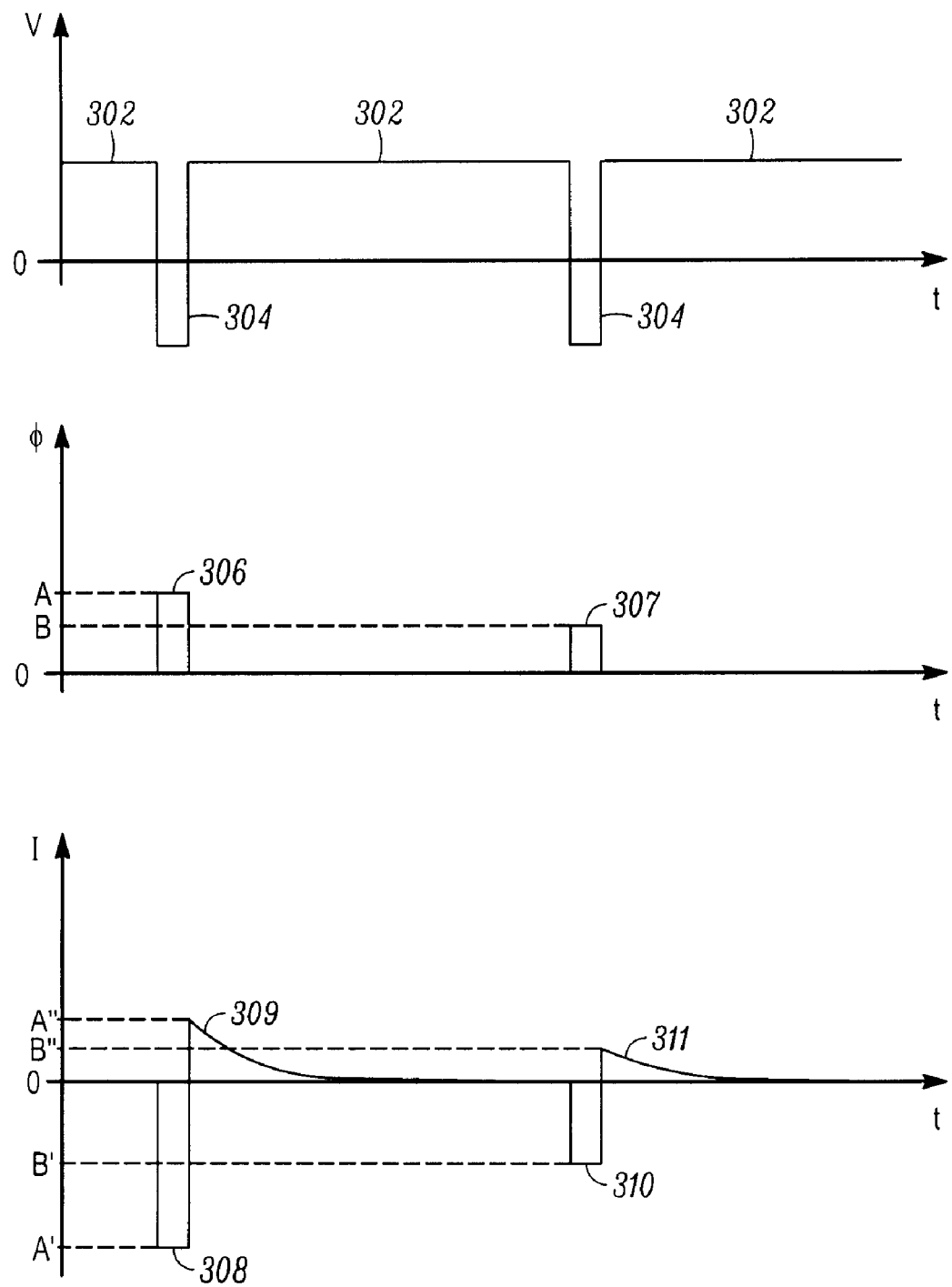
FIG. 3 is an illustration of waveforms in accordance with prior art techniques.
Figure 4:
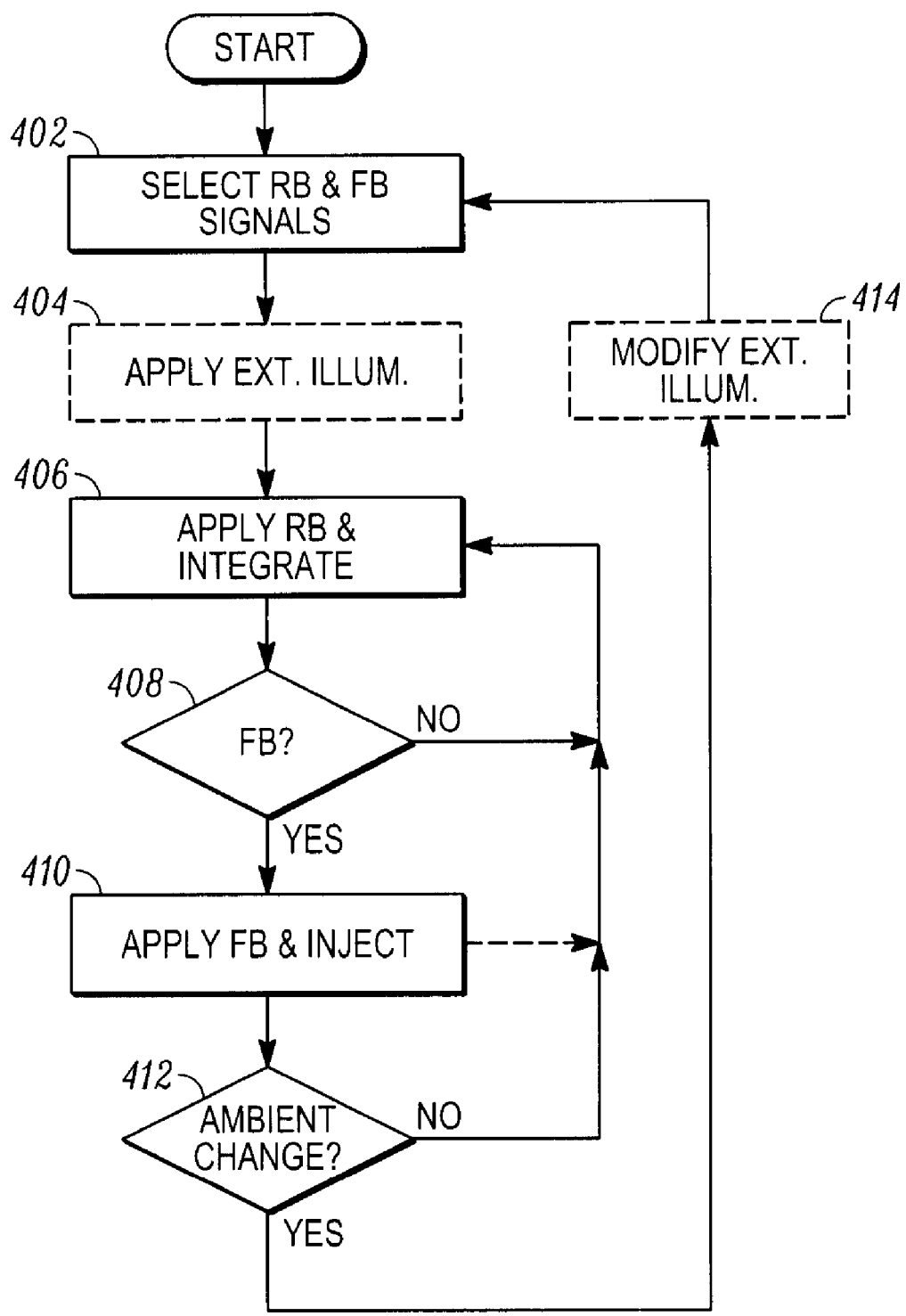
FIG. 4 is a flowchart illustrating operation of a retinal prosthesis system in accordance with the present invention.
Figure 5:
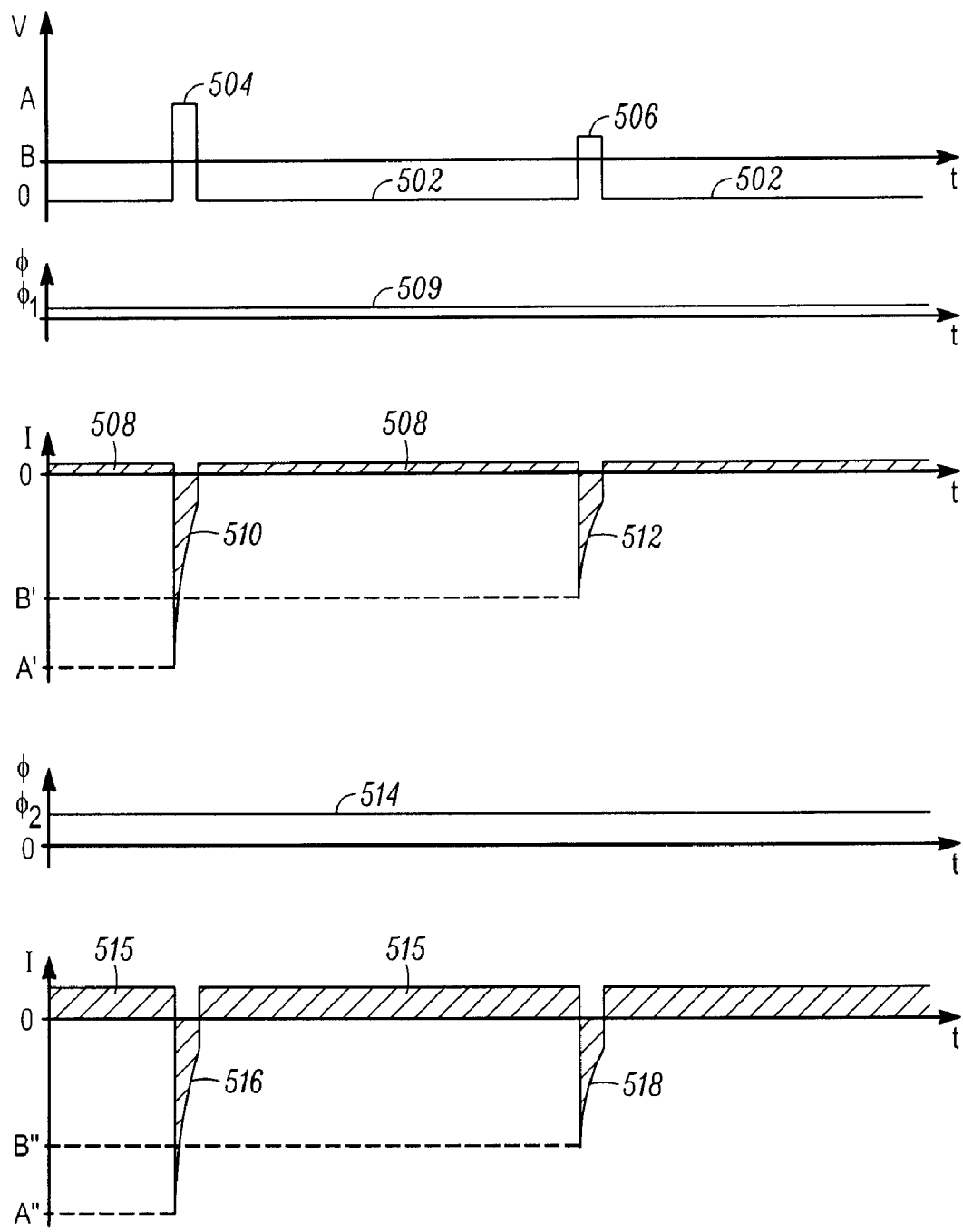
FIG. 5 is an illustration of waveforms further describing operation of a retinal prosthesis system in accordance with the present invention.

Referring now to FIGS. 3-5, operation of the present invention is further described and compared with prior art techniques. In FIG. 3, operation of a retinal prosthesis proposed by Palanker et al. in their paper "Design of a high-resolution optoelectronic retinal prosthesis", J. Neural Eng. 2 (2005) S105-S120 (hereinafter, "Palanker") is described. The scheme set forth in Palanker is premised on the concept of providing pulsed excitation both optically and electrically to a photodiode array of the type described above such that reverse-biasing of the photodiodes occurs in synchrony with the pulsed optical signals. Thus, as illustrated by the voltage waveform, V, a forward-bias signal 302 is provided to the photodiodes and, from time to time, a pulsatile reverse-bias signal 304 is also provided. During the reverse-bias pulses 304, the photodiodes operate in a photoconduction mode as noted above. Controlled optical pulses, whose intensity is illustrated by the waveform labeled $\phi$, are provided in synchrony with the pulsatile reverse-bias signals 304. Thus, the resulting current conducted by the photodiode (upon which the optical pulses 306, 307 are incident) will be directly proportional to the intensity of the incident optical pulse. This is illustrated in FIG. 3 where a first optical pulse 306 having a first amplitude, A, is provided resulting in a cathodic current 308 of amplitude A' and a subsequent anodic current 309 of amplitude A". In contrast, second optical pulse 307 having a second amplitude, B, which is less than the first amplitude A, results in a cathodic current 310 having amplitude B' less than amplitude A' and a subsequent anodic current 311 having amplitude B" less than amplitude A". Note that the areas beneath the cathodic current waveforms 308, 310 and their respective anodic current waveforms 309, 311 are substantially identical, thereby beneficially maintaining zero net charge injection over time. In summary, Palanker describes a system in which quantities of injected charge are determined by amplitudes of incident light pulses.

Referring now to FIG. 4, operation of the present invention is more fully described. Initially, the parameters for the reverse-bias signal 502 and the pulsatile forward-bias signal 504 are determined at step 402. In particular, the amplitudes for the signals 502, 504 are determined, as well as the timing of the pulsatile forward-bias signal 504. In a preferred embodiment, the voltages used must take into consideration the so-called "water window" which defines electrochemical potential limits within which the oxidation and reduction of water may be avoided. Exceeding these limits typically causes irreversible damage to the stimulating electrodes and may also cause harmful pH changes in the surrounding tissue. As known in the art, the anodic potential of the stimulating electrode should not exceed 0.8 V, and the cathodic potential should not exceed −0.6 V, each with respect to a Ag|AgCl reference. Additionally, the amplitude of individual pulses 504, 506 may be varied, as shown.

In a preferred embodiment, the pulsatile forward-bias signals 504 occur in a periodic manner at a fixed frequency and for specific durations. For example, it is expected that pulse repetition frequencies from 1 Hz to 50 Hz may be employed with pulse durations of not less than 0.1 milliseconds and not more than 100 milliseconds. Although the pulsatile forward-bias signals 504 are preferably provided at a fixed frequency, this is not a requirement and they may be provided in an aperiodic manner or at varying frequencies.

Referring again to FIG. 4, an optional step 404 of providing additional light, beyond ambient light, is shown. As described above, the Palanker method varies the amount of charge delivered by any individual photodiode by varying the amplitude of the light pulses delivered to that photodiode. In contrast, the present invention controls the amount of charge to be delivered by accumulating charge over time, which charge may be provided using nothing more than ambient light. However, it is recognized that in certain low light situations, it may be desirable to deliver additional light thereby enabling sufficient charge accumulation. Beneficially, such additional illumination, which is preferably in the infrared portion of the spectrum and delivered using glasses or goggles as described above, may be continuous rather than pulsed.

At step 406, the reverse-bias signal 502 is applied to the at least one photojunction element causing the stimulating element to operate in a photoconduction mode and thereby integrate current over time. The process of accumulating charge results from the manner in which electrodes exchange charge with biological tissue. As known in the art, stimulating electrodes of the type employed in the present invention establish a capacitive interface with the surrounding aqueous environment by the formation of a so-called "electrical double layer" and, in the case of iridium oxide electrodes, also through reversible valence transitions within the electrode material. The present invention exploits this capacitive property when the reverse-biased photojunction operates in a photoconductive mode whereby incident light generates a photocurrent that accumulates on the capacitance of the electrode and induces a concomitant change in the potential of the electrode. This is illustrated in FIG. 5 where, during application of the reverse-bias signal 502, an anodic charge 508 is built up over time. Note that the amplitude of the reverse-bias signal 502 affects the maximum level of charge accumulation; higher amplitudes lead to greater maximum charge levels and lower amplitudes lead to lesser maximum charge levels.

The process of accumulating charge continues until the charge capacity of the electrode is met or until a pulsatile forward-bias pulse 504 is applied, as shown at step 408. For example, as shown in FIG. 5, an anodic charge 508 is accumulated for the duration of each integration period. At step 410, the pulsatile forward-bias signal 504 is applied to the photojunction, establishing electrical continuity through the photojunction. This continuity results in a change in potential at the electrode causing the previously accumulated charge to be injected into the tissue as illustrated by the cathodic waveform 510, 512. The amplitude of the cathodic waveform 510 is determined by the amount of current accumulated during the integration period, which in turn depends on both the lighting conditions and the duration of the integration period. Additionally, the amplitude of the cathodic waveform 510 is controlled by the amplitude of the pulsatile forward-bias signal 504. This is illustrated in FIG. 5 where a first forward-bias pulse 504 of amplitude A results in a cathodic current having amplitude A'. In contrast, a subsequent forward-bias pulse 506 of amplitude B (less than A) results in a corresponding cathodic current having amplitude B' (less than A'). An illumination intensity $\phi_2$ shown in waveform 514, which is greater than the illumination intensity $\phi_1$ shown in waveform 509, results in a greater accumulation of charge 515 and a greater cathodic current with amplitude A" in pulse 516 larger than A' in 510. Note that the amplitude of the cathodic waveform 510, 512, does not depend significantly upon the amplitude of the incident light present during the forward-bias pulse, as in the Palanker method, but rather on the total amount of charge accumulated during the reverse-bias period, and on the amplitude of the forward-bias pulse 504. Thus, if, for a particular photojunction, an insufficient quantity of light is incident upon the photojunction in between applications of forward-bias pulses (i.e., during application of the reverse-bias signal) to establish accumulation of a sufficient amount of charge to reach the retinal stimulation threshold, the subsequent cathodic current will be insufficient to create a perceptual response. Conversely, a perceptual response will result if there is a sufficient quantity of light during the integration period to generate sufficient charge to reach the stimulation threshold. The charge capacity of the electrode should be large enough such that the full charge capacity of the electrode should be met only in relatively bright light conditions, and even then, only after substantially all of the integration period has passed. Stated another way, the electrode charge capacity shouldn't be so low, or the integration period so long, that even modest amounts of light will cause the capacity limit to be reached in a small fraction of the integration period. The electrode capacity should be large enough to allow for intermediate levels of light to accumulate charges to varying degrees above the stimulation threshold without reaching the charge capacity limit.

In a relatively simple implementation of the present invention, at the conclusion of the pulsatile forward-bias signal 504, 506, the reverse-bias signal 502 is again applied to the photojunction and the process described above is repeated, as illustrated by the dotted line exiting step 410. Referring again to FIG. 4, however, it is possible to ascertain, at step 412, whether ambient lighting conditions (specifically excluding any additional illumination applied, for example, as part of step 404) have changed to a sufficient degree to merit modifying any additional illumination being provided, or not, as the case may be. Changes to the overall ambient light conditions can be detected using additional photodetectors as known in the art, or by monitoring the current delivered by the pulse generator 240. The basis for using the charge delivered by the pulse generator as a measure of the ambient lighting conditions is that the total amount of charge supplied by the pulse generator during each forward-bias pulse will be substantially identical to the total amount of charge accumulated by all of the elements in the array 202 during the integration period, and therefore substantially proportional to the average illumination intensity on the array. If additional photodetectors are used, they may be deployed in such a manner that they are not influenced by any additional illumination provided. For example, the additional photodetectors may reside external to the body on the glasses or goggles used to support the additional illumination light source. The signal derived from photodetectors or from monitoring the pulse generator output may be used to test the ambient change condition set forth in step 412. For example, a decrease in the ambient light intensity may be used to cause an increase in the additional external illumination provided at step 414. Likewise, a sufficient increase in ambient illumination (for example, when a person walks out of a relatively dark indoor environment to a bright outdoor environment) may be used to cause the additional external illumination to be decreased or even terminated at step 414.

Additionally, changes to the ambient lighting may necessitate changes to the timing and amplitude parameters of the reverse-bias and pulsatile forward-bias signals, as described above at step 402. For example, when ambient light levels decrease, it may be desirable to decrease the frequency of the forward-bias pulses thereby allowing longer integration times. In brighter ambient conditions, it may be advantageous to decrease the amplitude of the forward-bias pulses thereby decreasing the amount of injected charge. In this manner, operation of the present invention may be refined to provide even greater control of a retinal prosthesis.

The present invention provides a technique for providing greater control over the quantities of electrical charge that may be delivered by a retinal prosthesis comprising photojunction elements, while still retaining the ability of such prostheses to exploit the natural movements and focusing ability of the eye. This is achieved through the application of reverse-bias signals that allow the photojunctions to operate in an integration mode whereby charges are accumulated over time. Application of subsequent forward-bias pulses cause the accumulated charge to be injected into the retinal tissue. By accumulating charge over a relatively long integration period and delivering the accumulated charge in a comparatively short interval, the present invention achieves stimulus currents that are substantially greater than the photocurrents generated by the incident light, and control over the stimulus currents is achieved through adjustment of the timing and amplitude of the forward- and reverse-bias pulses.

Although particular embodiments have been disclosed herein in detail, this has been done for purposes of illustration only and is not intended to be limiting with respect to the scope of the appended claims that follow. In particular, it is contemplated by the inventors that various substitutions, alterations, and modifications may be made to the invention without departing from the spirit and scope of the invention as defined by the claims. Other aspects, advantages, and modifications are considered to be within the scope of the following claims.

I claim:

1. A retinal prosthesis for stimulating a retina of an eye, comprising:
   at least one stimulating component, each stimulating component comprising:
      a photojunction element; and
      an electrode for electrical contact with tissues of the retina, the electrode being in electrical communication with the photojunction element via a first terminal of the photojunction element; and
   a pulse generation circuit, in electrical communication with a second terminal of the photojunction element, which provides a reverse-bias signal to the at least one photojunction element and which, from time to time, provides a pulsatile forward-bias signal to the at least one photojunction element, wherein the pulsatile forward-bias signal releases accumulated electrical charge into retinal tissues via said electrode to stimulate the retina.

2. The retinal prosthesis of claim 1, further comprising:
   an energy source in electrical communication with and providing power to the pulse generation circuit.

3. The retinal prosthesis of claim 2, the energy source further comprising a photovoltaic device.

4. The retinal prosthesis of claim 3, the photovoltaic device configured for intraocular implantation.

5. The retinal prosthesis of claim 2, the energy source further comprising a secondary inductive coil.

6. The retinal prosthesis of claim 1, further comprising:
   a plurality of stimulating components; and
   a common electrode in electrical communication with the pulse generation circuit and in electrical communication with the second terminal of each photojunction element of the plurality of stimulating components.

7. The retinal prosthesis of claim 6, further comprising:
   an insulating layer disposed over the common electrode to electrically insulate the common electrode from an environment surrounding the retinal prosthesis.

8. The retinal prosthesis of claim 6, wherein the pulse generation circuit comprises an extra-ocular pulse generation circuit, and further comprising:
   a conductive element, in electrical communication with the extra-ocular pulse generation circuit and the common electrode, for conveying the reverse-bias signal and the pulsatile forward-bias signal.

9. The retinal prosthesis of claim 1, wherein the photojunction element of each of the at least one stimulating component further comprises a photodiode.

10. The retinal prosthesis of claim 1, wherein the electrode of each of the at least one stimulating component is configured for implantation proximate to the retina.

11. The retinal prosthesis of claim 1, wherein the electrode of each of the at least one stimulating component further comprises an iridium oxide electrode.

12. A retinal prosthesis for stimulating a retina of an eye, comprising:
   a plurality of photodiodes;
   a plurality of iridium oxide electrodes, configured for implantation proximate to the retina, each in electrical communication with, via a first terminal of, a uniquely corresponding one of the plurality of photodiodes;
   a common electrode in electrical communication with a second terminal of each of the plurality of photodiodes; and
   a pulse generation circuit, in electrical communication with the common electrode, which provides a reverse-bias signal to the plurality of photodiodes and which, from time to time, provides a pulsatile forward-bias signal to the plurality of photodiodes to release accumulated electrical charge into retinal tissues via said plurality of iridium oxide electrodes to stimulate the retina.

13. The retinal prosthesis of claim 12, further comprising:
   an energy source in electrical communication with and providing power to the pulse generation circuit.

14. The retinal prosthesis of claim 13, the energy source further comprising a photovoltaic device.

15. The retinal prosthesis of claim 13, the energy source further comprising a secondary inductive coil.

16. The retinal prosthesis of claim 12, further comprising:
an insulating layer disposed over the common electrode to electrically insulate the common electrode from an environment surrounding the retinal prosthesis.

17. A method for stimulating a retina of an eye in which a retinal prosthesis comprising a photojunction element has been implanted proximate to the retina, the retinal prosthesis further comprising an electrode in electrical communication with a first terminal of the photojunction element, the method comprising:
applying a reverse-bias signal to the photojunction element;
while the reverse-bias signal is applied to the photojunction element, accumulating electrical charge through photoconduction resulting from light incident upon the photojunction element; and
from time to time, applying a pulsatile forward-bias signal to the photojunction element to establish electrical continuity in the photojunction, and thereby to inject the electrical charge into the retina via the electrode to provide a stimulus current.

18. The method of claim 17, further comprising:
controlling amplitude of the stimulus current by varying the duration of the reverse-bias signal.

19. The method of claim 17, further comprising:
controlling amplitude of the stimulus current by varying an amplitude of the pulsatile forward-bias signal.

20. The method of claim 17, further comprising:
applying light, beyond ambient light, to the photojunction element.

21. The method of claim 20, further comprising applying infrared light to the photojunction element.

* * * * *